United States Patent [19]

Gerhard

[11] 3,942,107
[45] Mar. 2, 1976

[54] METHOD AND APPARATUS EMPLOYING THIN CONDUCTIVE FILMS ON FLEXIBLE NONCONDUCTIVE SHEETS FOR NON-DESTRUCTIVE MEASUREMENT OF ELECTRICAL CHARACTERISTICS

[75] Inventor: Allen Robert Gerhard, Whitehall, Pa.

[73] Assignee: Western Electric Company, Inc., New York, N.Y.

[22] Filed: Aug. 26, 1974

[21] Appl. No.: 500,799

[52] U.S. Cl. .............................. 324/57 Q; 324/58 B
[51] Int. Cl.² ................... G01R 27/26; G01R 27/06
[58] Field of Search .... 324/57 Q, 58 R, 58 A, 58 B, 324/58 C; 100/211; 156/287

[56] References Cited
UNITED STATES PATENTS

| | | | |
|---|---|---|---|
| 1,806,861 | 5/1931 | Owen.................................. | 100/211 |
| 2,565,952 | 8/1951 | Curran et al........................ | 100/211 |
| 3,136,946 | 6/1964 | Le Vine............................ | 324/58.5 A |
| 3,510,764 | 5/1970 | Heath.............................. | 324/58.5 C |

OTHER PUBLICATIONS
Olyphant, Jr. et al, "Strip-line Methods for Dielectric Measurements at Microwave Frequencies", IEEE Trans. of Electrical Insulation, Vol. EI-5, 3-1970, pp. 26-32.

*Primary Examiner*—John K. Corbin
*Assistant Examiner*—Wm. H. Punter
*Attorney, Agent, or Firm*—G. W. Houseweart; M. Y. Epstein

[57] ABSTRACT

In a non-destructive, production-oriented technique for measuring an electrical characteristic of a material, a first nonconductive flexible sheet having a first conductive pattern thereon is pressed against a portion of the surface of the material, and a second nonconductive flexible sheet having a second conductive pattern thereon is pressed against another portion of the surface of the material. An electrical signal is applied between the two patterns and the effect of the material on the signal is measured to obtain a desired electrical characteristic of the material. The method and apparatus are particularly useful for measuring, at microwave frequencies, the propogation velocity factor and dielectric constant of substrates for use in thin film microwave circuits. For such measurements, the first and second conductive patterns advantageously comprise a resonant circuit and a ground plane. The measurement is made by applying a swept frequency signal to the resonant circuit while simultaneously monitoring reflected power from the resonant circuit.

9 Claims, 4 Drawing Figures

METHOD AND APPARATUS EMPLOYING THIN CONDUCTIVE FILMS ON FLEXIBLE NONCONDUCTIVE SHEETS FOR NON-DESTRUCTIVE MEASUREMENT OF ELECTRICAL CHARACTERISTICS

BACKGROUND OF THE INVENTION

1. Field of the Invention

This invention relates to a method and apparatus for precisely and non-destructively measuring an electrical characteristic of a material; and more particularly to measuring, at production-oriented speeds, properties such as propogation velocity factor and dielectric constant of thin film substrates at microwave frequencies.

Methods and apparatus for "production-oriented" testing advantageously have certain attributes which are different from the attributes of laboratory testing. For example, a production-oriented test technique should be capable of performance in a sufficiently short test time to be economically feasible. Of equal importance, or course, is that the production-oriented test be nondestructive. Another significant factor is that the test be sufficiently accurate, either in absolute accuracy or in calibratable repeatability. Also significant for a production-oriented test is that it provide measured values which indicate as directly as possible, without further computation, the desired characteristic which is being measured.

A particular testing problem arose from the following circumstances. It was known that electrical characteristics of microstrip circuits formed on thin film substrates, e.g., of alumina, are significantly dependent on two parameters, namely characteristic impedance and propogation velocity factor. These two parameters in turn are a function of the dimensions of the circuit applied to the substrate, the thickness of the substrate, and the dielectric constant of the substrate. One can readily calculate that for a substrate having a dielectric constant of about 10.0, a thickness of about 25 mils, and circuit line widths of about 25 mils, a 1 percent variation in either the line-width of the circuit applied to the substrate, the substrate thickness, or the dielectric constant will produce a 0.5% variation in characteristic impedance of the circuit applied to the substrate. Also, a one percent variation in either the line-width, the substrate thickness, or the dielectric constant will produce 0.36%, 0.05%, and 0.48% variation, respectively, in propogation velocity factor for a circuit formed on the substrate.

In view of the foregoing and in view of the tolerances which are often placed on microstrip circuits, a substrate is often required to meet a particular value of dielectric constant to within one percent. No production-oriented technique for measuring the dielectric constant or propogation velocity factor of substrates intended for use at microwave frequencies to the degree of accuracy is known.

2. Description of the Prior Art

One known technique for measuring dielectric constant with acceptable accuracy was reported by W. P. Harris and A. H. Scott in a report entitled "Precise Measurement of Dielectric Constant By The Two-Fluid Technique" in the *Proceedings of The National Bureau of Standards Conference on Electrical Insulation*, 1962, pages 51–53. This two-fluid technique involves doing four successive capacitance measurements at audio frequencies in two different fluids and then calculating the dielectric constant of the material from the capacitance measurements. This is not an acceptable production technique due to the considerable time required for the measurements and calculations and due to the complexity involved. Another problem with the two-fluid technique is that the dielectric constant of many materials of interest, e.g., aluminum oxide, varies with frequency. Thus, the effective dielectric constant at microwave frequencies is not the same as a measured value at an audio frequency.

Another known technique for measuring propogation velocity factor with acceptable accuracy was reported by H. F. Lenzing in a report entitled "Measurement of Dielectric Constant of Ceramic Substrates at Microwave Frequencies" presented at the Electronics Division, American Ceramic Society Meeting, Washington, D.C., May 10, 1972, Paper 41. The Lenzing technique consists of completely metallizing a substrate except for two very samll coupling slots and measuring the resonant frequencies of the rectangular cavity thus formed. The dielectric constant can then be calculated from the resonant frequencies measured and the length and width of the substrate. Unfortunately, this technique is both very time consuming and destructive, and so is not suitable for production-oriented testing.

SUMMARY OF THE INVENTION

In view of the aforementioned and other problems inherent in prior art methods and apparatus for measuring electrical characteristics of materials, it is an object of this invention of provide a new and improved method and apparatus for production-oriented testing.

It is a further object of this invention to provide a new and improved method and apparatus for measuring properties of materials at microwave frequencies.

It is a further object of this invention to provide a new and improved method and apparatus for nondestructively measuring an electrical characteristic of a material.

To these and other ends, a method for measuring an electrical characteristic of a material in accordance with this invention includes pressing a first nonconductive flexible sheet having a first conductive pattern thereon against a portion of the surface of the material and pressing a second nonconductive flexible sheet having a second conductive pattern thereon against another portion of the surface of the material. An electrical signal is applied between the two patterns and the effect of the material on the signal is measured to derive a number representative of the electrical characteristic being measured.

After the measurement has been completed, the sheets and patterns are removed from the material without damaging any significant attribute or characteristic of the material.

In practice, the conductive patterns may be between the sheets and the material when the sheets are pressed against the material or, optionally, for improved lifetime of the conductive patterns, the patterns may be on the side of the sheets away from the material.

Although it will be appreciated that the principles of this invention may be used for measurement of virtually any electrical characteristic of any material, for simplicity and clarity of explanation the invention will be described principally with reference to the measurement of electrical properties, such as propogation velocity factor and dielectric constant of thin film substrates at microwave frequencies. These electrical properties advantageously in accordance with this invention are measured by embodying the first conductive pattern in the form of a single port resonant circuit and the second conductive pattern in the form of a ground plane. The first and second nonconductive flexible sheets are pressed against the thin film substrate, for example with air pressure. The ground plane and resonant circuit may be either on the side of the sheet next to the substrate or on the side of the sheet away from the substrate.

A microwave signal of varying frequency is applied between the conductive pattern and ground plane, and the power reflected from the resonant circuit is monitored during the application of the microwave signal. The frequency at which maximum power absorption occurs in the resonant circuit is measured to provide an indication of the dielectric constant and propogation velocity factor for the substrate.

Also in accordance with this invention is apparatus for measuring an electrical characteristic of a material. The apparatus includes a first nonconductive flexible sheet having a first conductive pattern thereon and a second nonconductive flexible sheet having a second conductive pattern thereon. Expedients are included for pressing the sheets into contact with different portions of the surface of the material and for applying an electrical signal between the two patterns while monitoring the effect of the material on the signal.

BRIEF DESCRIPTION OF THE DRAWING

The aforementioned and other features, characteristics, and advantages, and the invention in general, will be better understood from the following more detailed description taken in conjunction with the accompanying drawing in which.

Figure 1:
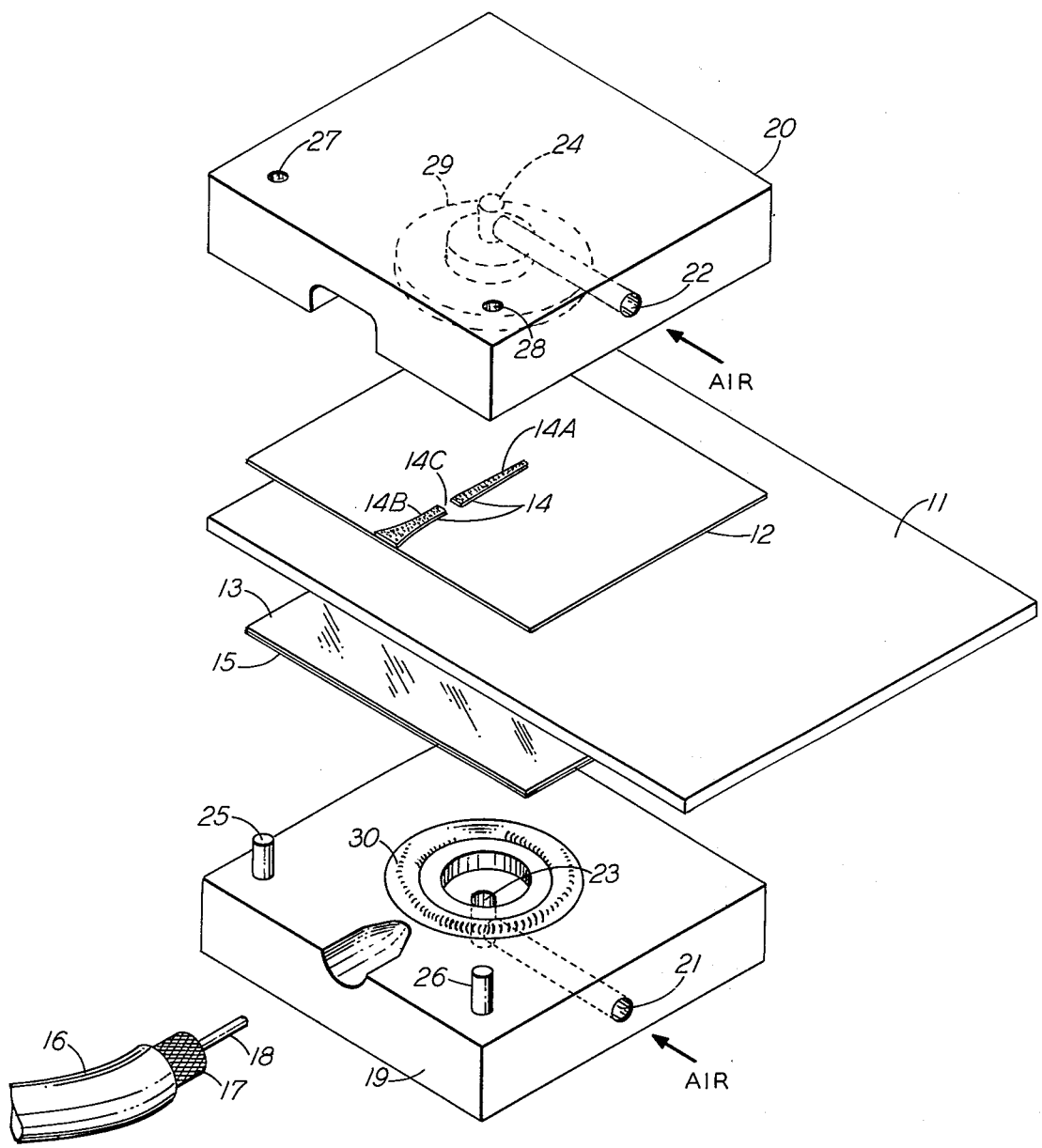
FIG. 1 is a somewhat schematic exploded mechanical diagram of apparatus for production-oriented electrical testing in accordance with this invention.

It will be appreciated that for simplicity and clarity of explanation, the figures of the drawing have not necessarily been drawn to scale.

DETAILED DESCRIPTION

With reference now to the drawing, FIG. 1 is a somewhat schematic mechanical diagram showing an exploded view of apparatus suitable for use in accordance with this invention. In FIG. 1 a thin film ceramic substrate 11, whose dielectric constant is to be measured, is shown. Such a ceramic typically will be of the order of 25 mils (0.025 inches) thickness and about 3.75 inches by 4.50 inches in lateral dimension and will typically be of alumina, the dielectric constant ($\epsilon$) of which is about 10.0. Features 12 and 13 in FIG. 1 are thin, nonconductive flexible sheets, e.g., a polyimide such as KAPTON about 1.0 mil thick.

Selectively formed on sheet 12, for example by electroless plating and/or electroplating, is a single port resonant circuit, designated generally as 14, including a half-wave stub portion 14A and a connection portion 14B, separated by a small air gap 14C. Sheet 13 has formed thereon, by a nonselective deposition process such as electroless plating and/or electroplating, a continuous ground plane 15 of a suitable conductive material such as gold or copper.

Figure 3:
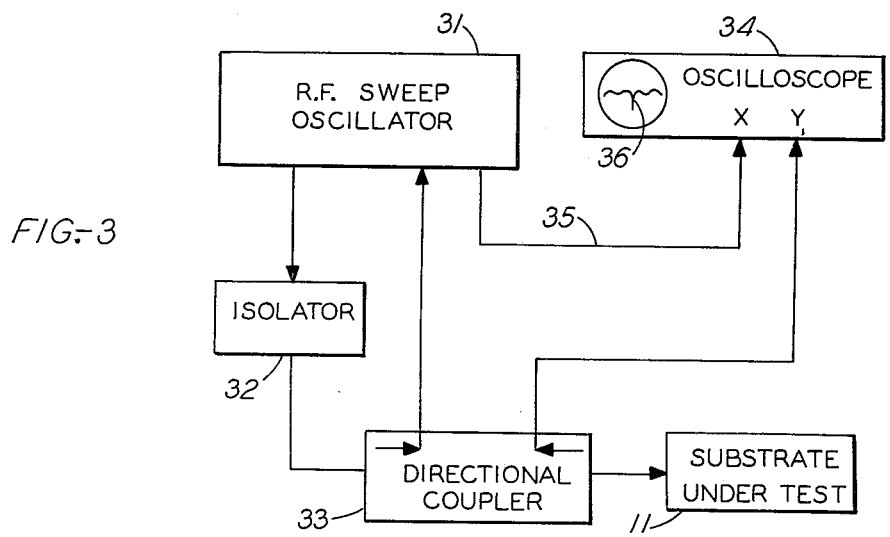
FIG. 3 is an electrical schematic block diagram of circuitry suitable for applying and measuring the electrical signals employed in the performance of this invention.

In operation sheets 12 and 13 with conductive patterns 14 and 15 thereon are pressed into intimate but detachable physical contact with substrate 11, and electrical signals are applied between patterns 14 and 15 to effect the measurement. The electrical signals are typically applied via a coaxial conductor 16 having its outer ground conductor 17 coupled to ground plane 15 and its inner, central, signal-carrying conductor 18 coupled to connector portion 14B of pattern 14. Circuitry suitable for applying microwave signals through the coaxial conductor 16 and for measuring power reflected from the resonant circuit is shown in FIG. 3 and will be described below in reference thereto.

For pressing the sheets with the conductive patterns thereon into the described physical contact with the substrate 11 to be tested, the apparatus of FIG. 1 includes a pair of opposed members 19 and 20 for pressing sheets 12 and 13 into contact with substrate 11. Members 19 and 20 include input ports 21 and 22 for receiving pressurized air which is applied through openings 23 and 24 to press sheets 12 and 13 against substrate 11. As can be seen in FIG. 1, member 19 also includes a pair of guide pins 25 and 26 adapted to mate with a pair of receiving holes 27 and 28, respectively, in member 20 for locating member 20 with respect to member 19.

To effect a test, member 20 is moved on pins 25 and 26 away from member 19 by an amount sufficient to permit insertion of substrate 11 and sheets 12 and 13. Member 20 is then moved on guide pins 25 and 26 toward member 19 and is clamped thereto by any suitable clamping mechanism (not shown). Air pressure is then applied through ports 21 and 22 and openings 23 and 24 to further press the sheets into intimate contact with substrate 11. Air pressures in the range of 10 to 30 pounds per square inch have been used. Thirty pounds per square inch is preferred.

After the test is complete, the air pressure is released and member 20 is physically declamped from and removed from member 19 by an amount sufficient to permit removal of substrate 11 therefrom.

Figure 2:
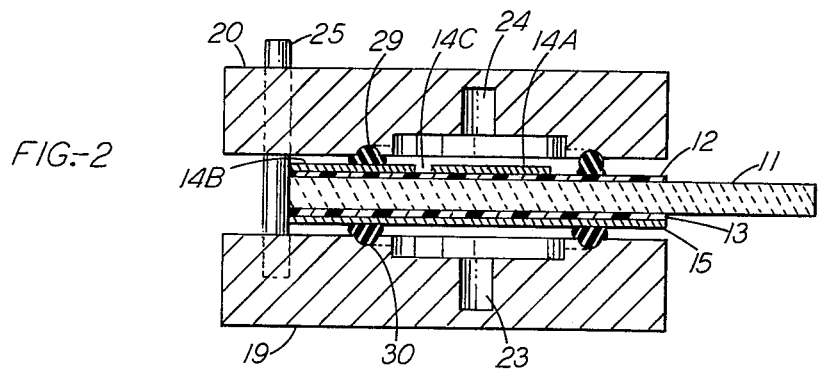
FIG. 2 is a cross-section of the apparatus of FIG. 1 as it appears in operation with the sheets pressed into engagement with the substrate.

FIG. 2 shows in cross section the apparatus of FIG. 1 as it appears in operation with the sheets pressed against the substrate 11. Shown in FIGS. 1 and 2 are O-rings 29 and 30 mounted in members 19 and 20 for pressing the sheets and patterns against substrate 11 to further insure a reliably intimate contact therewith. O-rings 29 and 30 may be any suitable resilient material such as neoprene or silicon rubber. Feature 29, of course, need not be an O-ring, and in the case of a simple straight line half-wave stub 14A, such as shown in FIG. 1, may advantageously be a rectangular annulus. It is illustrated as an O-ring in view of expected use with the more advantageous circular single port resonant pattern illustrated in FIG. 4, which will be described in detail below with reference thereto.

With reference now to FIG. 3 there is shown an electrical schematic diagram of circuitry suitable for applying test signals to and monitoring power reflected from the circuit of the apparatus of FIGS. 1 and 2 in accordance with this invention. As shown, a signal of varying microwave frequencies, typically termed a swept frequency, is applied by an RF sweep oscillator 31 through a suitable conventional isolator 32 and a directional coupler 33 to the substrate 11 under test. A portion of the power reflected from the resonant circuit 14A applied to the circuit under test is diverted by directional coupler 33 to the Y input of an oscilloscope 34. A voltage ramp proportional to the swept frequency from oscillator 31 is applied to the X input of oscilloscope 34 via a line 35. The RF signal from oscillator 31 is also diverted by directional coupler 33 back to a level control input of oscillator 31 to enable the oscillator to supply a constant level of signal to the substrate under test. This is important in practice because the reflected power to be measured should not be allowed to vary due to the level of the input signal.

During the test, the power reflected by the resonant circuit will undergo a minimum, designated 36 in FIG. 3, at the frequency where the single port resonant circuit experiences peak power absorption. Knowing this frequency, one can directly determine the propogation velocity factor of the substrate under test. Alternately, and more significantly, by inserting into the apparatus of FIGS. 1 and 2 a substrate whose propogation velocity factor or dielectric constant is known, one can calibrate the oscilloscope 34 so that the point 36 of peak power absorption is read out directly by an operator in terms of percentage frequency variation from a known value corresponding to the desired value of propogation velocity factor or dielectric constant.

Knowing percentage frequency variation, one can calculate a corresponding percentage variation for dielectric constant, according to the formula:

$$\left[\frac{\Delta \epsilon r}{\epsilon r}\right] = -2.1 \left[\frac{\Delta f_{res}}{f_{res}}\right]$$

where:

$\epsilon r$ = relative dielectric constant of a known substrate at a known resonant frequency ($f_{res}$) where peak power is absorbed;

$\Delta \epsilon r$ = variation from $\epsilon r$; and $\Delta f_{res}$ = variation from $f_{res}$.

Also, knowing frequency variation ($\Delta f_{res}$) and the resonant frequency ($f_{res}$) of a substrate having a known propogation velocity, the propogation velocity of another substrate can be determined according to the following relation:

$$\frac{\Delta V_m}{V_m} = \frac{\Delta f_{res}}{f_{res}}$$

where:

$V_m$ = propogation velocity on a known substrate; and
$\Delta V_m$ = variation from $V_m$ Of course, the foregoing formulas need not be used for each measurement. Rather, prior to production-oriented testing for "screening" acceptable substrates, one or both formulas are used to calculate a maximum allowable percentage variation in resonant frequency from known maximum allowable tolerances in dielectric constant and/or propogation velocity factor. Then with the oscilloscope calibrated with a known standard substrate, an operator merely needs to observe percentage frequency variation and whether it is within the previously calculated limits.

Figure 4:
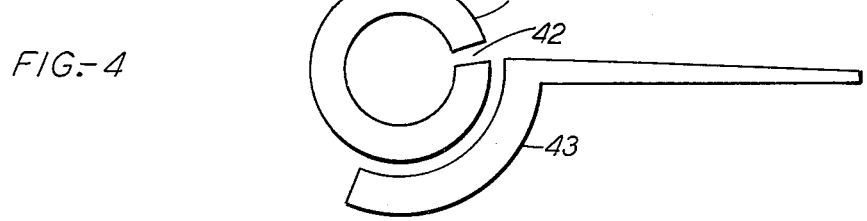
FIG. 4 is a plan view of an advantageous single port resonant circuit for use in measuring properties such as propogation velocity factor and dielectric constant at microwave frequencies in accordance with this invention.

A variety of suitable single port resonant circuits are possible and useful in apparatus such as that shown in FIGS. 1 and 2. A presently preferred one, shown in FIG. 4, includes a circular resonant pattern 41 capacitively coupled to an input connection portion 43. As seen, the resonant portion includes a nearly complete circle 41 having a small air gap 42 therein. The configuration of FIG. 4 is preferred principally because it permits measurement of a smaller area than does a straight line pattern such as illustrated in FIGS. 1 and 2. In practice, apparatus of the type depicted in FIG. 4 has been used with the line width of circular portion 41 being about 100 mils, the gap portion 42 being about 10 degrees or arc or a mean distance of about 50 mils, and the gap between input portion 43 and circular portion 41 being about 5 mils. From these given numbers it will be appreciated that FIG. 4 is not to scale insofar as the gap between input portion 43 and circular portion 41 is concerned.

Using apparatus of the type depicted in FIGS. 1–4, with a resonant circuit of the type depicted in FIG. 4, an accuracy of about ± 0.05% with respect to repeatability in resonant frequency has been obtained. Such as accuracy enables corresponding determination of dielectric constant with a repeatability of about ±0.1%, which is more than adequate for any foreseeable production-oriented need at the present time.

As was alluded to hereinabove, a significant advantage of the inventive apparatus is that the propogation velocity factor or dielectric constant of a relatively small area can be measured. With apparatus of the type described herein, measurements at 28 different locations on a substrate of about 3.75 × 4.50 inches have been made, enabling a determination of the variation in dielectric constant across such substrates. Such measurements have proved very useful in demonstrating that the variation across a substrate can be significantly greater than expected and could thus cause deleterious inaccuracies in circuits manufactured on such substrates wherein it had been assumed that the average dielectric constant was within the specified 1% range.

Although the invention has been described in part by making detailed reference to certain specific embodiments, such detail is intended to be, and will be understood to be, instructive rather than restrictive. It will be appreciated by those in the art that many variations may be made in the structure and modes of operation without departing from the spirit and scope of the invention as disclosed in the teaching contained herein.

For example, it will be appreciated that the resonant circuit may be adapted to operate as a band pass filter, in which case transmitted power rather than reflected power could be measured.

Further, it will be appreciated that a great variety of different conductor pattern structures may be used on the flexible sheets, depending upon the particular type of electrical characteristic to be measured.

Further, or course, a great variety of different materials may be used for the flexible sheets themselves, depending upon the particular attributes which the worker in the art may desire.

What is claimed is:

1. A method for measuring an electrical characteristic of a material comprising the steps of:
    pressing with fluid pressure applied and distributed against a first nonconductive flexible sheet having a first conductive pattern adhered thereto into intimate but releasable contact with a portion of the surface of the material;

pressing with fluid pressure applied and distributed against a second nonconductive flexible sheet having a second conductive pattern adhered thereto into intimate but releasable contact with another portion of the surface of the material;

applying an electrical signal between the two patterns; and sensing the effect of the material on the signal.

2. A method as recited in claim 1 wherein the sheets are pressed into contact with the material such that the first sheet is between the first pattern and the material and the second sheet is between the second pattern and the material.

3. A method as recited in claim 1 wherein the sheets are pressed into contact with the material such that the first pattern is between the first sheet and the material and the second pattern is between the second sheet and the material.

4. A method as recited in claim 1 wherein the material is a plane dielectric and the electrical characteristic is propogation velocity factor.

5. A method as recited in claim 1 wherein the fluid pressure is air pressure.

6. Apparatus for measuring an electrical characteristic of material comprising:

a first nonconductive flexible sheet having a first conductive pattern thereon;

a second nonconductive flexible sheet having a second conductive pattern thereon;

means for receiving a pressurized fluid and for distributing said fluid against the sheets for pressing the sheets into contact with different portions of the surrface of the material;

means for applying an electrical signal between the two patterns while the sheets are pressed against the material; and means for sensing the effect of the material on the signal.

7. Apparatus as recited in claim 6 wherein the pressing means includes means for pressing the sheets into contact with the material such that the first pattern is between the first sheet and the material and the second pattern is between the second sheet and the material.

8. Apparatus as recited in claim 6 wherein the pressing means includes means for pressing the sheets into contact with the material such that the first sheet is between the first pattern and the material and the second sheet is between the second pattern and the material.

9. Apparatus as recited in claim 6 wherein the pressurized fluid is pressurized air.

* * * * *